United States Patent [19]

Inazawa

[11] Patent Number: 5,741,649
[45] Date of Patent: Apr. 21, 1998

US005741649A

[54] METHOD AND KIT FOR DETECTING BREAST CANCER CELLS

[75] Inventor: Johji Inazawa, Kyoto, Japan

[73] Assignee: Daikin Co., Ltd., Osaka, Japan

[21] Appl. No.: 625,213

[22] Filed: Apr. 1, 1996

[30] Foreign Application Priority Data

Apr. 2, 1995 [JP] Japan .................................. 7-112217
Sep. 8, 1995 [JP] Japan .................................. 7-231556

[51] Int. Cl.$^6$ .............................. C12Q 1/68; C12P 19/34; C07H 21/02; C07H 21/04
[52] U.S. Cl. ........................ 435/6; 435/91.2; 536/23.1; 536/24.3; 536/24.33; 536/26.6
[58] Field of Search .................... 435/6, 91.2; 536/23.1, 536/24.3, 33, 26.6

[56] References Cited

U.S. PATENT DOCUMENTS 5,545,527  8/1996  Stevens et al. .................................. 435/6

FOREIGN PATENT DOCUMENTS

94/13834  6/1994  WIPO.

OTHER PUBLICATIONS

Sato et al, "Allelotype of Breast Cancer: Cumulative Allele Losses Promote Tumor Progression in Primary Breast Cancer", Cancer Res. 50, pp. 7184–7189, 1990.

Takita et al, "Correlation of Loss of Alleles on the Short Arms of Chromosomes 11 and 17 with Metastasis of Primary Breast Cancer to Lymph Nodes", Cancer Res. 52, pp. 3914–3917, 1992.

Bieche et al, "Two Distinct Regions Involved in 1p Deletion in Human Primary Breast Cancer", Cancer Res. 53 pp. 1990–1994, 1993.

Winqvist et al, "Refinement of Regional Loss of Heterozygosity for Chromosome 11p15.5 in Human Breast Tumors", Cancer Res., pp. 4486–4488, 1993.

Chen et al, "Deletion of Two Separate Regions on Chromosome 3p in Breast Cancers", Cancer Res. 54, pp. 3021–3024, 1994.

Waye et al, "Chromosone–Specific Alpha Satellite DNA from Human Chromosome 1: Hierarchical Structure and Genomic Organization of a Polymorphic Domain Spanning Several Hundred Kilobase Pairs of Centromic DNA", Genomics 1, pp. 43–51, 1987.

Inazawa et al, "Assignment of the Human Granulocyte Colony–Stimulating Factor Receptor Gene (CSF3R) to Chromosome 1 at Region p 35–p 34.3", Genomics 10, pp. 1075–1078, 1991.

Inazawa et al, "High–Resolution Cytogenetic Mapping of 342 New Cosmid Markers Including 43 RFLP Markers on Human Chromosome 17 by Fluorescence in Situ Hybridization", pp. 153–162, 1993.

Jones et al, "Detection of Loss of Heterozygosity at the Human TP53 Locus Using a Dinucleotide Repeat Polymorphism", Genes, Chromosomes and Cancer. pp. 89–90, 1992.

Isomura et al, "Detailed Analysis of Loss of Heterozygosity on Chromosome Band 17p13 in Breast Carcinoma on the Basis of a High–Resolution Physical Map With 29 Markers", Genes, Chromosomes and Cancer, pp. 173–179, 1994.

Strawbridge et al, "Role of Cytology in Management of Lesions of the Breast", Surg. Gynecol. & Obstet., vol. 152, No. 1 pp. 1–7, 1981.

Miki et al, "A Strong Candidate for the Breast and Ovarian Cancer Susceptibilty Gene BRCA 1", Science, vol. 266, pp. 66–71, 1994.

Tokino et al, "Isolation and Mapping of 62 New RFLP Markers on Human Chromosome 11", Am. J. Hum. Genet., vol. 48, pp. 258–268, 1991.

Tanigami et al, "Mapping of 262 DNA Markers into 24 intervals on Human Chromosome 11", Am. J. Hum. Genet., vol. 50, pp. 56–64, 1992.

Takahashi et al, "R–banding and nonisotopic in situ hybridization: precise localization of the human type II collagen gene (COL 2A1)",Hum. Genet. vol 86, pp. 14–16, 1990.

Gyapay et al, "The 1993–94 Généthon human genetic linkage map". Nature Genetics, vol. 7, 1994, pp. 247–249.

Cooke et al, "Cloning of human satellite III DNA: different components are on different chromosomes", Nucleic Acids Research, vol. 6, No. 10, 1979, pp. 3177–3197.

Waye et al, "Organization and evolution of alpha satellite DNA from human chromosome 11", Chromosoma, vol. 95, pp. 182–188.

Waye et al, "Structure, Organization, and Sequence of Alpha Satellite DNA from Human Chromosome 17: Evidence for Evolution by Unequal Crossing–Over and an Ancestral Pentamer Repeat Shared with the Human X Chromosome", Mol. and Cell. Bio. p. 3156–3165, 1986.

"Molecular Cloning: A Laboratory Manual", Cosmid Vectors, pp. 3.27–3.53 2nd ed., 1989.

Pinkel et al, "Cytogenic analysis using quantitative, high–sensitivity, fluorescence hybridization", Proc. Natl. Acad. Sci. USA, vol. 83, pp. 2934–2938, 1986.

Harrison et al, "Chromosome 1 Aneusomy, Identified by Interphase Cytogenics, in Mammographically Detected Ductal Carcinoma in situ of the Breast", Journal of Pathology, vol. 175, pp. 303–309, 1995.

Verdoodt et al, "Improved detection of DNA aneuploidy in primary breast cancer using quantitative DNA image analysis in combination with fluorescent in situ hybridization technique", Hist. J., vol. 27. pp. 79–88. 1995.

(List continued on next page.)

*Primary Examiner*—W. Gary Jones
*Assistant Examiner*—Dianne Rees
*Attorney, Agent, or Firm*—Foley & Lardner

[57] ABSTRACT

A method and kit for detecting breast cancer cells is disclosed, which is not only as convenient and noninvasive as conventional cytological examination, but also is more accurate and objective than cytological examination. The invention establishes a method for detecting breast cancer cells, wherein the method judges cells examined to be breast cancer cells when aneusomy is detected on 1) either chromosome 1 or chromosome 11 or both, 2) either chromosome 1 or chromosome 17 or both or 3) at least any one of chromosomes 1, 11 and 17 of the cell sample.

17 Claims, No Drawings

OTHER PUBLICATIONS

Murphy et al, Interphase Cytogenetic Analysis of erbB2 an topoIIα Co-amplification in Invasive Breast Cancer and Polysomy of Chromosome 17 in Ductal Carcinoma *in situ*, Int. J. Cancer, vol. 64, pp. 18–26, 1995.

Devilee et al, "Detection of Chromosome Aneuploidy in Interphase Nuclei from Human Primary Breast Tumors Using Chromosome–specific Repetitive DNA Probes", pp. 5825–5830, 1988.

Loupart et al. "Confirmation of the copy number of chromosome 1 in interphase nuclei from paraffin sections of breast tumours by fluorescence *in situ* hybridization", Chromosome Res., vol. 3, 410–416, 1995.

Dhingra et al, "Chromosome *in situ* hybridization on formalin–fixed mammary tissue using no–isotopic, non–fluorescent probes: technical considerations and biological implications", Breast Cancer Research and Treatment, vol. 23, pp. 201–210, 1992.

Micale et al, "Chromosomal Aneuploidy in Proliferative Breast Disease", Human Pathology, vol. 25, No. 1, pp. 29–35, 1994.

Waldeman et al. Proc. Annu Meet. Am Assoc Cancer Research 32: pp.A179, 1991.

Deville et al. Cancer Research 48: 5825–5830 1988.

METHOD AND KIT FOR DETECTING BREAST CANCER CELLS

FIELD OF THE INVENTION

The present invention relates to a method for determining whether a human cell sample contains breast cancer cells or not by detecting aneusomy on 1) chromosomes 1 and 11, 2) chromosomes 1 and 17 or 3) chromosomes 1, 11 and 17, and relates to a method for detecting breast cancer cells when aneusomy is found on 1) either chromosome 1 or chromosome 11 or both, 2) either chromosome 1 or chromosome 17 or both or 3) at least any one of chromosomes 1, 11 and 17, and also a kit for practicing said method.

BACKGROUND OF THE INVENTION

Morbidity and mortality of breast cancer in Japan are increasing each year partially due to the westernization of living environment including the eating habits. The toll taken by breast cancer has surpassed that taken by uterine cancer, and breast cancer is expected to become the first cause of cancer mortality in Japanese women in the near future.

Diagnosis of breast cancer is generally initiated by inspection and palpation for any abnormality such as a tumor, followed by imaging comprising mammography, ultrasonic examination and thermography, cytologic examination using mamilla secretions, punch aspiration tissue samples, mammary duct rinses, sponge biopsy samples from erosive mamilla and mamma areola and smears obtained by pressing tissue excised by surgical operation, pathological examination such as biopsy, and immunological examination using tumor markers.

However, since diagnosis of cancer by imaging and tumor markers is indirect and supplementary, it is difficult to accurately determine whether the cell sample is benign or malignant. Therefore, diagnostic results on morphological irregularity, extent of infiltration, etc. based on the cytologic examination using punch aspiration tissue samples are highly important.

However, evaluation of malignancy based on cytologic examination differs somewhat from one examiner to the other, lacking objectivity. Accordingly, the judgement of malignancy greatly relies on the experience of a limited number of skilled experts, and accuracy of detecting tumor cells is not necessarily high. False negativity rate of cytologic examination using punch aspiration tissue sample is reported to be more than 10% (H. Strawbridge et al., Surg. Genecol. Obstet., 152, 1, 1981). Accordingly, when malignancy is judged to be at the stage of class II~III, it is actually fairly difficult for physicians to decide on a suitable treatment thereafter.

On the other hand, it has been demonstrated that, in the carcinogenic process, multistage abnormality develops in a plurality of genes, and accumulation thereof leads to the acquisition of biological as well as clinical malignant character by the cell. These findings indicate that it is possible not only to detect cancer cells accurately but also the stage of cancer cells in their multistage carcinogenic process and evaluate the degree of malignancy of cancer cells by determining amplification of known oncogenes, excessive expression of oncogene products, lack of a region on a chromosome wherein tumor suppressor genes are assumed to be present, and excessive alteration of various chromosomes.

As oncogenes relating to breast cancer, c-myc, erbB, erbB2 and PRAD1 have been recognized. Since amplification of these oncogenes and excessive expression of the oncogenes' products are observed in breast cancer tissues, a close relationship is indicated between variation of these oncogenes and the degree of tumor malignancy as well as prognosis of the disease. In addition, as the candidate of breast cancer suppressor gene, p53, Rb, NM23, prohibitin, BRCA1 etc. have been isolated (K. Takita et al., Tanpakushitsu-Kakusan-Koso, 38, 305, 1993; Y. Miki et al., Science, 266, 66, 1994).

In the case of breast cancer, loss of heterozygosity has been reported on 1p, 1q, 3p, 11p, 13q, 16q and 17p (T. Sato et al., Cancer Res., 50. 7184, 1990; K. Takita et. al., Cancer Res., 52, 3914, 1992; I. Bieche et al., Cancer Res., 53, 1990, 1993; R. Winqvis et al., Cancer Res., 53, 4486, 1993; L. C. Chen et al., Cancer Res., 54, 3021, 1994). Also, the correlation of a lack of 11p and 17p with metastasis of breast cancer to lymph node has been suggested (K. Takita et al., Cancer Res., 52, 3914, 1992). On 17p, lack of the telomere region (17p13.3) rather than p53 region is related to metastasis to lymph node. Link analysis revealed that the gene causing proleptic hereditary breast cancer is located in the q arm of chromosome 17 (17q21) (K. Takita et al., Tanpakushitsu-Kakusan-Koso, 38, 305, 1993; Y. Miki et al., Science, 266, 66, 1994). However, the correlation between abnormality of each chromosome and incidence of breast cancer is not sufficiently high enough (about 50 odd percent at most). Since it is difficult to determine whether the cell sample is benign or malignant by detecting abnormality of each gene for each case, no practical method for detecting breast cancer with high accuracy has yet been developed along this line.

Thus, there is a great need for establishing simple and highly accurate methods for detecting breast cancer cells which allow application for clinical test.

SUMMARY OF THE INVENTION

The present invention aims to provide a simple, speedy and highly accurate method for detecting breast cancer cells which allows practical application to the clinical test of said cells.

DETAILED DESCRIPTION OF THE INVENTION

By the term "aneusomy" used in the present specification is meant monosomy (lack of one chromatid, resulting in one chromatid in a particular chromosome within the cell) or polysomy (increase in one or more chromatids, resulting in more than three chromatids in a particular chromosome within the cell).

Lack of a segment of the q arm of chromosome 17 (17p13.3) which was reported to correlate with metastasis of breast cancer to lymph node was investigated with punch aspiration tissue samples from breast cancer of patients in 20 cases (comprising 7 cases of benign tumor and 13 cases of malignant tumor). The size of tumors ranged from a minimum of 12×12 mm to a maximum of 50×30 mm. Samples were examined following signals generated by double target polychromatic FISH (K. Matsubara et al. (eds.), Jikkenkogaku, Supplement, Experimental Protocol Series, "FISH Experimental Protocol," p.128, Shujunsha, 1994) using a YNZ22 cosmid marker (17p13.3) newly isolated (M. Isomura et al., Genes Chromosomes Cancer, 9, 173, 1994) and 17q11 (cCI17-321) marker as the probes. No lack of 17p13.3 was observed at all with benign tumor samples. On the other hand, lack of 17p13.3 was observed in high frequency in 8 out of 13 cases (67%) of malignant tumors and in 6 cases (75%) was linked with metastasis to lymph nodes. Metastasis to lymph nodes was also observed in 2 out of 4 cases (50%) which had been judged not lacking 17p13.3. Furthermore, LOH was examined with some of these samples using microsatellite markers TP53 (17p13.1) (M. H. Jones et al., Genes Chromosomes Cancer, 5, 89, 1992) and AFM207Xa11 (17p13.3) (G. Grapay et al., Nat. Genetics, 7, 246, 1994). Of cases with results obtained, no LOH was present in cases wherein no lack of 17p13.3 had been observed by the FISH method, while LOH was confirmed using either one of two markers in cases wherein lack of 17p13.3 had been detected. These results indicate that lack of the gene in question can be determined accurately by the FISH method performed with a minute quantity of the sample taken directly from tumors by punch aspiration.

Next, aneusomy on chromosomes 1, 11 and 17 was examined with similar punch aspiration tissue samples (comprising 15 cases of benign tumor and 60 cases of malignant tumor added to said 7 cases of benign tumor and 13 cases of malignant tumor described above totaling 22 cases of benign tumors and 73 cases of malignant tumors, corresponding to cases 1~6 in Table 1) by the FISH method using the probes specific for the centromere region of each chromosome (pUC1.77, cCR11 and cCI17-321). To the inventors' surprise, while no aneusomy was observed on these three chromosomes of benign tumors at all, abnormality was detected on either one of chromosomes 1 and 11 or both in 68 out of 73 cases of breast cancer (93.2%), and on either one of chromosomes 1 and 17 or both in 67 out of 73 cases of breast cancer (91.8%). That is, the present inventors discovered that breast cancer cells can be identified in a human cell sample when aneusomy is detected on either one of chromosomes 1 and 11 or both, or either one of chromosomes 1 and 17 or both of the sample, accomplishing the present invention. Furthermore, the present inventors found that aneusomy was detected on at least one of chromosomes 1, 11 and 17 of the human cell samples examined in 70 out of 73 cases (95.9%). That is, the present inventors also found that breast cancer cells can be identified when aneusomy was detected on at least any one of chromosomes 1, 11 and 17 of the human cell samples. Furthermore, out of 73 cases of breast cancer, aneusomy was detected on chromosome 1 in 64 cases (87.7%), chromosome 11 in 48 cases (65.8%), and chromosome 17 in 38 cases (52.1%). These results indicate that accurate detection of breast cancer cells cannot be made by examining aneusomy of each chromosome singularly.

In three cases (breast cancer case nos. 2, 4 and 5 in the first Example) which were judged to be of class III by the conventional cytologic examination method prior to operation, breast cancer cells were also detected by the present detection method. Furthermore, in two cases (benign tumor cases nos. 6 and 77 in the first Example) of intraductal papilloma which was notorious as one of the most difficult breast cancers to be diagnosed, the cells which had been judged to be of class IV by the conventional cytologic examination could be accurately determined to be benign cells.

Mamilla secretions, punch aspiration tissue samples, mammary duct rinses, sponge biopsy samples from erosive mammilla and mamma areola and smear biopsy samples from tissue excised by surgical operation, etc. can be used as the sample for FISH method performed of the present invention. Preferably these samples contain at least 100 cells or more. In the case of liquid samples, cells contained in the sample may be recovered by centrifugation, if necessary, prior to the test. Then, according to the standard method, cells are fixed with organic solvents (alcohols such as methanol, ethanol, etc.), acid (acetic acid) or cross-linkage reagents (formalin, paraformaldehyde, glutaraldehyde, etc.), etc. It is preferable to fix cells with a mixture of acetic acid/methanol (1/3). Cells may be subjected to a hypotonic treatment with 0.075M KCl etc. prior to the fixation by standard methods. Fixed cells can be subjected to various fluorescence in situ hybridization reactions after they are dispersed in solution or spread on slide glass. Although the fluorescence in situ hybridization method (FISH) is preferable, simultaneous detection by the polychromatic fluorescence in situ hybridization (FISH) method using probes with various different ligands or labels and comprising nucleotide sequences specific to 1) chromosomes 1 and 11, 2) chromosomes 1 and 17 or 3) chromosomes 1, 11 and 17, respectively, is more convenient. Various techniques of FISH including the polychromatic fluorescence in situ hybridization method are described in detail in Saibokogaku, Experimental Protocol Series, "FISH Experimental Protocols" (K. Matsubara et al. (eds.), Shujunsha, 1994).

There is no limitation to probes used for practicing the FISH method of the present invention, and those having nucleotide sequences specific to chromosomes 1, 11 and 17, respectively may be used. For example, probes specific to respective chromosomes, such as painting probes (e.g., Whole Chromosome Painting System, BRL, Inc.), various satellite DNAs (I, II, III, IV, α, β, etc.), probes comprising telomere sequences (e.g., available from ONCOR Inc., etc.) and other locus specific probes can be used. Preferable probes specific to chromosome 1 are those prepared from plasmid pUC1.77 comprising the chromosome 1 specific satellite III DNA sequence (H. J. Cooke et al., Nucleic Acids Res., 6, 3177, 1979) and plasmid pSD1-1 containing chromosome 1 specific α satellite DNA (J. W. Waye et al., Genomics, 1, 43, 1987). Preferable probes specific to chromosome 11 are those prepared from plasmid cCR11 (see Example 1) and plasmid pLC11A comprising chromosome 11 specific α-satellite DNA (J. S. Waye et al., Chromosoma, 95, 182, 1987). Preferable probes specific to chromosome 17 are those prepared from plasmid cCI17-321 (J. Inazawa et al., Genomics, 17, 153, 1993) and plasmid p17H8 comprising chromosome 17 specific α-satellite DNA (J. S. Waye et al., Mol. Cell. Biol., 6, 3156, 1986).

To prepare ligand-binding or labeled probes, nick translation and random primer methods are commonly used. Preferred ligands which can link to specific reporter molecules are biotin, digoxigenin or a mixture thereof (biotin and digoxigenin). Alternatively, probes which contain biotin and digoxigenin, respectively, are separately prepared and the mixture thereof can be used as the probe containing both ligands (K. Matsubara et al. (eds.), Saibokogaku Supplement, Experimental Protocol Series "FISH Experimental Protocol," p.128, Shujunsha, 1994). After hybridization with these ligands described above, the detection is carried out by reacting said ligands with avidin, streptoavidin or anti-digoxigenin antibody labeled with fluorescers. Alternatively, each probe may be separately and directly labeled beforehand with fluorescein isothiocyanate, carboxymethylindocyanin succinimidyl ester, rhodamine, Texas Red (sulforhodamine), tetramethylrhodamine isothiocyanate or 7-amino-4-methylcumarin-3-acetic acid.

The present invention can be carried out also by Southern hybridization of the DNA extracted from cells by standard methods prior to fixation using polytypic markers which are suitable for detecting aneusomy on 1) chromosomes 1 and 11, 2) chromosomes 1 and 17 or 3) chromosomes 1, 11 and 17.

Furthermore, the present invention can be carried out also by hybridization of the DNA extracted from cells by standard methods prior to fixation using minisatellite or microsatellite markers which are suitable for detecting aneusomy on 1) chromosomes 1 and 11, 2) chromosomes 1 and 17, or 3) chromosomes 1, 11 and 17.

However, in the course of development of the present invention, some cases which had been judged lacking 17p13.3 by the FISH method, for example, were judged in the contrary not lacking 17p13.3by LOH detection with microsatellite marker using the DNA extracted from excised tumors as the template because of the contamination of normal cells which made it difficult to determine whether said 17p13.3 was present or absent.

Therefore, after the locus dense with tumor components was identified by preparing a hematoxylin-eosin stained sample from the same tumor and then the tumor tissue was isolated precisely from a paraffin block of the sample, the lack of 17p13.3 was definitely re-confirmed by the LOH assay with said recovered sample. Recently, the LOH detection method using a polytypic microsatellite has been introduced as a gene diagnosis technique because it is more convenient than the conventional Southern hybridization method. However, since judgement of LOH assay becomes difficult due to the contamination of the isolated tumor sample with normal cells, in some cases, it might be judged "not lacking," that is, false negative. These results indicate that, in the daily clinical assay with a minute quantity of tumor sample routinely supplied, analysis of chromosomal abnormality using microsatellite marker has problems in its accuracy. Methods for detecting tumor cells by the FISH method will certainly overcome these problems.

The present invention also relates to a kit for the simple, speedy and highly accurate detection of breast cancer cells. Said kit of the present invention may comprise the following reagents:

1) a probe specific to chromosome 1, 2) a probe specific to chromosome 11, 3) hybridization fluid, 4) rinse solution, and 5) staining fluid;

2) a probe specific to chromosome 1, 2) a probe specific to chromosome 17, 3) hybridization fluid, 4) rinse solution and 6) staining fluid; or 3) a probe specific to chromosome 1, 2) a probe specific to chromosome 11, 3) a probe specific to chromosome 17, 4) hybridization fluid, 5) rinse solution and 6) staining solution.

EXAMPLES

The present invention will be described in detail with reference to the following examples which are for illustrative purposes and should not be regarded as limiting the scope of invention.

Example 1

1) Preparation of samples

Samples were obtained by standard punch aspiration of benign tumors in 7 cases and malignant tumors in 14 cases, in total 21 cases, using 21-gauge syringe needles. Punch aspiration samples thus obtained were transferred into Eppendorf tubes containing 75 mM KCl (0.1 ml) and incubated at room temperature for 30 min. Cells were then fixed by the addition of an equal volume of Carnoy's fixing fluid (acetic acid:methanol=1:3) and centrifuged to remove the supernatant. Sedimented cells were re-suspended in Carnoy's fixing fluid, dropped onto slide glass, fixed by flame or air drying, and finally dried at 70° C. for 5 h.

2) Isolation of cosmid clone cCR11 containing nucleotide sequence specific to the centromere region of chromosome 11

Cosmid clone cCR11 containing a nucleotide sequence specific to the centromere region of chromosome 11 was isolated according to the method of Tanikami et al. (A. Tanikami et al., Am. J. Hum. Genet., 50, 56, 1992; A. Tanikami et al., Tanpakushitsu, Kakusan, Koso, 38, 244, 1993; M. Hori and Y. Nakamura (eds.), Labomanual Human Genome Mapping, p.41, Maruzen, 1991).

First, cosmid libraries were prepared from the chinese hamster×human hybrid cell line containing a single human chromosome 11 DNA in a hamster genomic background (T. Tokino et al., Am. J. Hum. Genet., 48, 258, 1991). That is, the genomic DNA was extracted from said cell, partially digested with restriction enzyme Sau3AI and subjected to sucrose density gradient (10%–30%) centrifugation to obtain fractions containing 35–45 kb DNA fragments. The cleaved termini of said fragments were partially filled in by the action of Klenow enzyme in the presence of dATP and dGTP. DNA fragments thus obtained were cleaved with restriction enzyme XhoI, and said cleaved termini were inserted by ligation reaction to the termini of cosmid vector pWEX15 partially filled in by the action of Klenow enzyme in the presence of dCTP and dTTP.

Cosmid libraries were prepared by packaging of the DNA obtained by ligation using GIGAPACK II GOLD11™ (Strategene Inc.). $E.$ $coli$ strain 490A infected with the cosmid thus obtained (50 µ g/ml) was inoculated on LB agar medium containing ampicillin and incubated at 37° C. overnight (so as to form about $2 \times 10^4$ colonies per plate). Then, clones containing the DNA derived from human chromosome 11 were detected by colony hybridization using 32P-labeled human genomic DNA as probe (Cot1 DNA/GIBCO BRL). Positive clones were isolated and incubated on 96-well microplates. Cosmid clones comprising the inserted DNA derived from human chromosome 11 thus obtained were isolated and purified by standard methods (J. Sambrook et al., "Molecular Cloning: A Laboratory Manual," 2nd Ed., Cold Spring Harbor Laboratory Press, 1989).

Loci of DNA fragments derived from chromosome 11 which were contained in the cosmid clone thus obtained were analyzed by the FISH method to Inazawa et al. (Genomics, 10, 1075, 1991; Genomics, 17, 153, 1993).

First, the sample of replicated prometaphase R-banded chromosomes was prepared by a thymidine synchronization/BrdU release method (a method that synchronizes cells with thymidine prior to incorporation of BrdU into replicating DNA) (E. Takahashi et al., Hum. Genet., 86, 14, 1990). Then, the chromosome slides were denatured in 70% formamide/2×SSC (consisting of 0.3M NaCl and 0.03M sodium citrate) at 75° C. for 2~5 min. After the slides were soaked in 70% ethanol at −20° C. for 3 min, they were dehydrated in an ethanol series.

Various cosmid DNA probes thus obtained were labeled with biotin-16-dUTP (Boehringer) by the standard nick-translation method (K. Matsubara et al. (eds.), Saibokogaku Supplement, Experimental Protocol Series, "FISH Experimental Protocol," Part 2, Section 2, Shujunsha, 1994). To the labeled cosmid probe were added sonicated salmon sperm DNA and $E.$ $coli$ tRNA. After the mixture was recovered by precipitation with ethanol, it was dissolved in formamide.

To each biotin-labeled cosmid probe fluid (50 ng/ml, 9 µl) was added Cot-1DNA (GIBCO BRL) (5 mg/ml, 1 µl). The mixture thus obtained was denatured at 70° C. for 10 min.

and then cooled on ice for 5 min. To the cooled mixture was added an equal volume of 20% dextran sulfate/4×SSC. After prehybridization at 37° C. for 20 min, this hybridization fluid was dropped onto the previously denatured slides described above, covered with parafilm and hybridized at 37° C. for 16~48 h in a sealed humidified chamber. After the slides were rinsed with 50% formamide/2×SSC, 2×SSC and 1×SSC respectively at 42° C. for 15 min each, they were incubated with 1% BLOCKACE™ (Danihon Pharmaceutical) containing avidin-FITC (5 µg/ml) (Boehringer)/4×SSC at 37° C. for 40 min. Then, the slides were rinsed with 4×SSC, 4×SSC/0.05% Triton X-100 and 4×SSC, respectively, at room temperature for 10 min. After the intensity of biotin-linked fluorescence signal was amplified by adding biotinylated anti-avidin antibody and avidin-FITC (D. Pinkel et al., Proc. Natl. Acad. Sci. USA, 83, 2934, 1986), an anti-fade solution containing 1% DABCO (1,4-diazabicyclo[2,2,2]octane) (Sigma) with PI (propidium iodide) (1 µg/ml) being dissolved therein was added to the slides, which were covered with cover slips and examined under a fluorescence microscope FXA (Nikon). PI-stained R-bands and FISH signals on chromosomes were observed through a Nikon B-2A filter.

By analysis with the FISH method described above, the cosmid clone comprising DNA sequences specific to the centromere region of chromosome 11 was isolated. Furthermore, Southern hybridization performed by standard methods using human genomic DNA with cCR11 as a probe revealed that cCR11 has tandem repeat sequences.

3) Preparation of probes pUC1.77 comprising the centromere-specific region of chromosome 1 (H. J. Cooke et al., Nucleic Acids Res., 6, 3177, 1979) and cCR11 comprising the centromere-specific region of chromosome 11 (K. Matsubara et al. (eds.), Saibokogaku Supplement, Experimental Protocol Series, "FISH Experimental Protocol," Part 2, Sections 2 and 11, Shujunsha, 1994) were labeled by nick-translation with biotin-16-dUTP. Similarly, cCI17-321 comprising the centromere-specific region of chromosome 17 was labeled by nick-translation with digoxigenin-11-dUTP (Boehringer). To the labeled probes were added sonicated salmon sperm DNA and *E. coli* tRNA, followed by ethanol, and precipitates thus recovered were dissolved in formamide.

4) In situ hybridization (polychromatic FISH)

The hybridization protocol followed that of K. Matsubara et al. (eds.) (Saibokogaku Supplement, Experimental Protocol Series, "FISH Experimental Protocol," Part 2, Sections 2 and 11, Shujunsha, 1994).

Slides prepared in 1) were denatured in 70% formamide/2×SSC at 75° C. for 4 min, soaked in 70% ethanol at −20° C. for 2~5 min, and then dehydrated in an ethanol series.

Biotin-labeled cCR11 probe fluid (50 ng/µl) and digoxigenin-labeled cCR11 probe fluid (50 ng/µl) were mixed in a ratio of 7:3 (cCR11 biotin/digoxigenin mix). Then biotin-labeled pUC1.77 probe fluid (50 ng/ml), digoxigenin-labeled cCI17-321 probe fluid (50 ng/µl) and cCR11 biotin/digoxigenin mix (50 ng/µl) were combined in a ratio of 2:4:3 (by volume). To the mixture (9.0 µl) was added Cot-1DNA (5 mg/ml) (1 µl), and the final mixture was denatured at 70° C. for 10 min, cooled on ice for 5 min, and then an equal volume of 20% dextran sulfate/4×SSC was added thereto. After prehybridization at 37° C. for 20 min, this hybridization fluid was dropped onto the denatured slides described above, covered with parafilm, and hybridized at 37° C. for 24~48 h in a sealed humidified chamber.

After slides were rinsed at 42° C. with 50% formamide/2×SSC, 2×SSC and 1×SSC respectively for 15 min each, they were incubated with 1% BLOCKACE™ (Dainihon Pharmaceutical) containing avidin-FITC(5 µg/ml) (Boehringer) and Rhodamine-anti-digoxigenin antibody (1 µg/ml) (Boehringer)/4×SSC at 37° C. for 40 min. Then slides were rinsed with 4×SSC, 4×SSC/0.05% Triton X-100 and 4×SSC respectively at room temperature for 10 min each. To slides was added anti-fade solution containing 1% DABCO (1,4-diazabicyclo[2,2,2]octane (Sigma) with DAPI (4,6-diamidino-2-phenylindole) (1 µg/ml) being dissolved therein, and slides were covered with cover-slips and observed under a fluorescence microscope FXA (Nikon). Through a UV-2A filter, DAPI-stained, undamaged metaphase nuclei not contacting each other were screened, and with more than 100 complete metaphase nuclei, signals derived from three probes were separately counted using a double-band pass filter (Omega Optics). Signals derived from the centromere region of chromosome 1 were detected as green spots (FITC), those of chromosome 11 as red spots (rhodamine) and those of chromosome 17 as yellow spots (false yellow synthesized from fluorescence of FITC and rhodamine). When metaphase nuclei having an abnormal number of signals derived from respective probes were present in more than 20% of the total nuclei examined, chromosomes were judged to have aneusomy. Results are shown in Tables 1 and 2, with those of benign tumors shown in Table 1 and those of malignant tumors in Table 2.

TABLE 1

Benign tumor

| Case | Histology [1] | Cytologic examination [2] | Aneusomy (chromosomes 1/11/17) [3] |
|---|---|---|---|
| 1 | Mastopathy | Class I | (−/−/−) |
| 2 | Fibroadenoma | Class II | (−/−/−) |
| 3 | Fibroadenoma | Class III | (−/−/−) |
| 4 | Fibroadenoma | Class II | (−/−/−) |
| 5 | Fibroadenoma | Class III | (−/−/−) |
| 6 | Intraductal papilloma | Class IV | (−/−/−) |
| 7 | Intraductal papilloma | Class IV | (−/−/−) |

TABLE 2

Breast cancer

| Case | TNM [4] | Lymph node [5] metastasis | Cytologic examination | Histology | Aneusomy (chromosomes 1/11/17) |
|---|---|---|---|---|---|
| 1 | T2 | n(+) | Class V | Pt [6] | (+/+/+) |
| 2 | T2 | n(−) | Class III | Pt | (+/−/−) |
| 3 | T2 | n(−) | Class V | M [7] | (+/−/+) |
| 4 | T3 | n(−) | Class III | Pt | (+/−/−) |
| 5 | T1 | n(+) | Class III | Sci [8] | (+/−/+) |
| 6 | T1 | n(+) | Class IV | Pt | (+/+/+) |
| 7 | T2 | n(−) | Class V | Pt | (+/+/−) |
| 8 | T2 | n(+) | — | Sci | (+/+/−) |
| 9 | T2 | n(+) | Class V | Lo [9] | (+/−/+) |
| 10 | T1 | n(+) | Class V | Sci | (−/+/−) |
| 11 | T1 | n(+) | Class V | Sci | (+/+/+) |
| 12 | T2 | n(+) | Class V | St [10] | (+/+/−) |
| 13 | T2 | n(−) | Class V | St | (+/+/+) |
| 14 | T1 | n(−) | Class V | St | (+/−/+) |

The numbered symbols used in Tables 1 and 2 mean the following:

TABLE 2-continued

Breast cancer

| Case | TNM [4] | Lymph node [5] metastasis | Cytologic examination | Histology | Aneusomy (chromosomes 1/11/17) |
|------|---------|---------------------------|----------------------|-----------|-------------------------------|

[1] Results of histological examination of samples of tumors excised by surgical operation. Samples which were finally diagnosed benign and malignant by this examination were described as benign tumors and breast cancers, respectively;
[2] Cytologic examination with samples obtained by punch aspiration;
[3] "+" and "−" denote the presence and absence of aneusomy, respectively;
[4] Stage classification according to UICC (Union internationale contre le cancer) (TNM classification);
[5] "n(+)" and "n(−)" denote the presence and absence of metastasis to the lymph nodes respectively;
[6] Papillotubular carcinoma;
[7] Medullary carcinoma;
[8] Scirrhous carcinoma;
[9] Invasive lobular carcinoma; and
[10] Solid tubular carcinoma.

Example 2

1) Preparation of samples

Similarly as described in Example 1, two slides each of every sample were prepared from 74 cases in total including 15 cases of benign tumors (Table 3) and 59 cases of malignant tumors (Tables 4–6) which were not included in Example 1.

2) Preparation of probes pUC1.77 containing the centromere-specific region of chromosome 1 (H. J. Cooke et al., Nucleic Acids Res., 6, 3177, 1979) and cCI17-321 containing the centromere-specific region of chromosome 17 were labeled by nick-translation with biotin-16-dUTP according to standard methods (K. Matsubara et al. (eds.), Saibokogaku Supplement, Experimental Protocol Series, "FISH Experimental Protocol," Part 2, Sections 2 and 11, Shujunsha, 1994). Similarly, cCR11 containing the centromere-specific region of chromosome 11 was labeled by nick-translation with digoxigenin-11-dUTP (Boehringer). To said labeled probes were added sonicated salmon sperm DNA and E. coli tRNA, and the mixture was recovered by ethanol precipitation and dissolved in formamide.

3) In situ hybridization

Hybridization was performed in essentially the same manner as described in 4) of Example 1 except for excluding the tri-color FISH method using three different probes at one time. Of two slides prepared per sample as described in 1), one slide was subjected to a two-color FISH assay for detecting aneusomy on chromosomes 1 and 11 using probes specific to chromosomes 1 and 11. Then, another slide was subjected to a FISH method for detecting aneusomy on chromosome 17 using a probe specific to chromosome 17.

One of two slides prepared from one sample as described in 1) was denatured in 70% formamide/2×SSC at 75° C. for 2~5 min, soaked in 70% ethanol at −20° C. for 3 min, and then dehydrated in an ethanol series. Biotin-labeled pUC1.77 probe solution and digoxigenin-labeled cCR11 probe solution were mixed in a ratio of 2:7 (V/V), and to this mixture (9.0 μl) was added Cot-1DNA (5 mg/ml) (1.0 μl). After the final mixture was denatured at 70° C. for 10 min, it was cooled on ice for 5 min, and to this mixture was added an equal volume of 20% dextran sulfate/4×SSC. After prehybridization at 37° C. for 10~20 min, this hybridization fluid was dropped onto the slide previously denatured as described above, covered by parafilm, and subjected to hybridization at 37° C. for 24~48 h in a sealed humidified chamber. After rinsing with 50% formamide/2×SSC at 37° C. for 15 min, followed by 2×SSC and 1×SSC at room temperature for 15 min each, the slide was incubated with 1% BlockaceTM (Dainihon Pharmaceutical) containing avidin-FITC (5 μg/ml) (Boehringer) and rhodamine-anti-digoxigenin antibody (1 μg/ml) (Boehringer)/4×SSC at 37° C. for 40 min. Then after washing with 4×SSC, 4×SSC/0.05% Triton X-100 and 4×SSC at room temperature for 10 min each, an anti-fade solution containing 1% DABCO (1,4-diazabicyclo[2,2,2]octane) (Sigma) with DAPI (4,6-diamidino-2-phenylindole) being dissolved therein was added to the slide, which was covered with a coverslip, and observed with a fluorescence microscope FXA (Nikon). Through a UV-2A filter, DAPI-stained and physically undamaged metaphase nuclei which were not touching each other were screened, and with 100 or more complete metaphase nuclei, signals derived from said two probes were counted using a double band pass filter (Omega Optical). Signals derived from the centromere region of chromosomes 1 and 11 are detected as green (FITC) and red (rhodamine) spots, respectively. When 20% or more of the metaphase nuclei examined had abnormal numbers of signals derived from each probe, the sample was judged to have aneusomy on its chromosomes.

Next, the other slide was denatured in 70% formamide/2×SSC at 75° C. for 2~5 min, soaked in 70% ethanol at −20° C. for 3 min, and then dehydrated in an ethanol series. To a solution (9.0 μl) consisting of biotin-labeled cCI17-321 probe fluid (30 ng/μl) (3 μl) and formamide (6.0 μl) was added Cot-1DNA (5 mg/ml) (1.0 μl), and this mixture was denatured at 70° C. for 10 min, and cooled on ice for 5 min. To the resultant mixture was added an equal volume of 20% dextran sulfate/4×SSC. After prehybridization at 37° C. for 10~20 min, this hybridization fluid was dropped onto the previously denatured sample slide described above, which was covered with parafilm and subjected to hybridization at 37° C. for 24~48 h in a sealed humidified chamber. After washing with 50% formamide/2×SSC at 37° C. at 15 min, followed by rising with 2×SSC and 1×SSC at room temperature for 15 min each, the slide was incubated in 1% Blockace (Dainihon Pharmaceutical) containing avidin-FITC (5 μg/ml) (Boehringer)/4×SSC at 37° C. for 40 min. Then the slide was rinsed with 4×SSC, 4×SSC/0.05% Triton X-100 and 4×SSC, respectively at room temperature for 10 min each. After the addition of anti-fade solution containing DAPI (4,6-diamidino-2-phenylindole) (1 μg/ml) dissolved in 1% DABCO (1,4-diazabicyclo[2,2,2]octane) (Sigma), the slide was covered with a coverslip and examined with a fluorescence microscope FXA (Nikon). Through a UV-2A filter, DAPI-stained and physically undamaged metaphase nuclei which were not touching each other were screened, and with 100 or more complete nuclei signals derived from the cCI17-321 probe were counted using a B-2E filter. Signals derived from the centromere of chromosome 17 were detected as green spots (FITC). When 20% or more of metaphase nuclei examined showed abnormality in signal numbers derived from the cCI17-321 probe, the sample was judged to have aneusomy.

Results of FISH analysis of these two slides are shown in Tables 3~6, with the results of benign tumors shown in Table 3 and those of breast cancers in Tables 4~6.

TABLE 3

Benign tumor

| Case | Histology | Aneusomy (chromosomes 1/11/17) |
|---|---|---|
| 1 | Fibrocystic disease | (–/–/–) |
| 2 | Mastopathy | (–/–/–) |
| 3 | Fat necrosis | (–/–/–) |
| 4 | Fibroadenoma | (–/–/–) |
| 5 | Fibroadenoma | (–/–/–) |
| 6 | Fibroadenoma | (–/–/–) |
| 7 | Fibroadenoma | (–/–/–) |
| 8 | Fibroadenoma | (–/–/–) |
| 9 | Fibroadenoma | (–/–/–) |
| 10 | Fibroadenoma | (–/–/–) |
| 11 | Fibroadenoma | (–/–/–) |
| 12 | Fibroadenoma | (–/–/–) |
| 13 | Fibroadenoma | (–/–/–) |
| 14 | Adenoma | (–/–/–) |
| 15 | Papillary hyperplasia | (–/–/–) |

TABLE 4

Breast cancer

| Case | TNM [4] | Lymph node metastasis [5] | Histology [1] | Aneusomy (chromosomes [3] 1/11/17) |
|---|---|---|---|---|
| 1 | T1 | n(–) | Pt [6] | (+/–/+) |
| 2 | T1 | n(–) | Pt | (+/+/+) |
| 3 | T2 | n(–) | St [10] | (+/+/+) |
| 4 | T1 | n(–) | Sci [8] | (–/–/+) |
| 5 | T2 | n(–) | Sci | (+/+/–) |
| 6 | T2 | n(–) | Pt | (+/–/–) |
| 7 | T4 | n(+) | Sci | (–/–/+) |
| 8 | T2 | n(–) | Pt | (+/+/+) |
| 9 | T2 | n(–) | Pt | (+/–/–) |
| 10 | T3 | n(+) | St | (+/+/+) |
| 11 | T1 | n(–) | Pt | (–/+/–) |
| 12 | T1 | n(+) | Sci | (+/+/–) |
| 13 | T1 | n(+) | St | (–/+/+) |
| 14 | T2 | n(+) | St | (+/+/–) |
| 15 | T1 | n(+) | St | (+/+/+) |
| 16 | T3 | n(+) | Pt | (+/+/+) |
| 17 | T1 | n(–) | St | (+/+/+) |
| 18 | T2 | n(+) | Pt | (+/–/+) |
| 19 | T1 | n(–) | Sci | (+/+/–) |
| 20 | T4 | n(–) | Pt | (+/+/+) |
| 21 | T2 | n(–) | Sci | (+/+/–) |
| 22 | T2 | n(–) | M [7] | (+/+/–) |
| 23 | T1 | n(–) | St | (–/–/–) |

TABLE 5

| Case | TNM | Lymph node metastasis | Histology | Aneusomy (chromosomes 1/11/17) |
|---|---|---|---|---|
| 24 | T1 | n(–) | Pt | (+/–/–) |
| 25 | T2 | n(+) | St | (+/–/–) |
| 26 | T2 | n(+) | Pt | (+/–/–) |
| 27 | T4 | n(+) | Pt | (+/+/–) |
| 28 | T2 | n(–) | Sci | (+/–/–) |
| 29 | T2 | n(+) | Pt | (+/+/+) |
| 30 | T2 | n(+) | Pt | (–/–/–) |
| 31 | T1 | n(–) | Sci | (+/–/–) |
| 32 | T2 | n(+) | Pt | (+/+/+) |
| 33 | T2 | n(–) | St | (+/+/+) |
| 34 | T2 | n(+) | St | (+/+/+) |
| 35 | T1 | n(+) | St | (+/+/+) |
| 36 | T1 | n(+) | Sci | (+/+/+) |
| 37 | T2 | n(–) | Pt | (+/+/–) |
| 38 | T2 | n(+) | St | (+/+/–) |
| 39 | T1 | n(–) | Pt | (–/+/+) |
| 40 | T4 | n(+) | Pt | (+/+/+) |
| 41 | T4 | n(+) | Sci | (+/+/+) |
| 42 | T1 | n(+) | Sci | (+/+/+) |
| 43 | T2 | n(–) | St | (+/+/+) |
| 44 | T2 | n(+) | Sci | (+/+/+) |
| 45 | T4 | n(+) | Pt | (+/+/+) |
| 46 | T4 | n(+) | M | (+/+/+) |
| 47 | T1 | n(–) | Pt | (–/–/–) |
| 48 | T2 | n(–) | Pt | (+/+/+) |

TABLE 6

| Case | TNM | Lymph node metastasis | Histology | Aneusomy (chromosomes 1/11/17) |
|---|---|---|---|---|
| 49 | T2 | n(–) | Sci | (+/+/–) |
| 50 | T2 | n(+) | Pt | (+/+/+) |
| 51 | T2 | n(+) | Pt | (+/+/+) |
| 52 | T2 | n(–) | Mu [11] | (–/+/–) |
| 53 | T2 | n(–) | St | (+/+/–) |
| 54 | T2 | n(–) | Sci | (+/+/–) |
| 55 | T2 | n(+) | Sci | (+/+/+) |
| 56 | T1 | n(–) | Sci | (+/–/–) |
| 57 | T1 | n(–) | Pt | (+/+/+) |
| 58 | T1 | n(+) | Mu | (+/+/–) |
| 59 | T1 | n(+) | St | (+/–/–) |

Numbered symbols used in Tables 4–6 have the same meaning as those in Tables 1 and 2, except that the following symbol was newly added.

11) Mucinous carcinoma

Summarizing the results shown in Tables 1–6, it has become evident that, in 22 cases of benign tumors, no aneusomy was observed at all on these three different chromosomes by the detection method of the present invention, while, out of 73 cases of breast cancer, aneusomy was found on either chromosome 1 or chromosome 11 or both in 68 cases (93.2%), and on either chromosome 1 or chromosome 17 or both in 67 cases (91.8%). Therefore, these results confirmed that, when aneusomy is detected on chromosome 1 or chromosome 11 or both, or chromosome 1 and chromosome 17 or both of the cell samples to be examined, cells can be judged to be breast cancer cells. It has also been demonstrated that, in 70 of said 73 cases of breast cancer, aneusomy was present in at least any one chromosome out of chromosomes 1, 11 and 17 of the cell samples. Thus, it has also been proved that, when aneusomy is detected on at least any one chromosome out of chromosomes 1, 11 and 17 of the cell samples, the cells can be judged to be breast cancer cells.

ADVANTAGE OF THE INVENTION

By the present invention it became possible to judge whether the cell samples are breast cancer cells or not by detecting aneusomy on 1) chromosomes 1 and 11, 2) chromosomes 1 and 17 or 3) chromosomes 1, 11 and 17 of the cells contained in mamilla secretions, punch aspiration tissue samples, mammary duct rinses, sponge biopsy samples from erosive mamilla and mamma areola or smear biopsy samples from tissue excised by surgical operation. That is, by the present invention, when aneusomy is detected on 1) either chromosome 1 or chromosome 11 or both, 2)

either chromosome 1 or chromosome 17 or both, or 3) at least any one of chromosomes 1, 11 and 17 of the cell sample, the cells are judged to be breast cancer cells. Thus, the present invention provides a method for detecting breast cancer cells which is not only as convenient and noninvasive as the conventional cytologic examination but also far more accurate and objective than the cytologic examination.

The disclosures of all references cited above are expressly incorporated herein by reference in their entireties. The disclosures of Japanese Patent Applications Nos. JP 7/112217 (filed on Apr. 2, 1995) and JP 7/231556 (filed on Sep. 8, 1995), respectively, for which benefit under 35 U.S.C. § 119 is claimed, are expressly incorporated herein.

It will be apparent to those skilled in the art that various modifications and variations can be made to the methods and kits of this invention. Thus, it is intended that the present invention cover such modifications and variations, provided they come within the scope of the appended claims and their equivalents.

What is claimed is:

1. A method for detecting breast cancer cells, consisting essentially of hybridizing a sample from human breast tissue with probes which specifically hybridize with two chromosomes, said two chromosomes being chromosomes 1 and 11 or chromosomes 1 and 17, and identifying the sample to contain breast cancer cells when aneusomy is observed on either chromosome 1 or chromosome 11 or both, or either chromosome 1 or chromosome 17 or both of the sample.

2. A method for detecting breast cancer cells, consisting essentially of hybridizing a sample from human breast tissue with probes which specifically hybridize with chromosomes 1, 11, and 17, and identifying the sample to contain breast cancer cells when aneusomy is observed on any one chromosome or combination of at least two chromosomes selected from the group consisting of chromosomes 1, 11 and 17 of the sample.

3. The method for detecting breast cancer cells according to claim 1, wherein said cell sample is derived from mammilla secretions, punch aspiration tissue samples, mammary duct rinses, sponge biopsy samples of erosive mammilla and mamma areola or smears obtained by pressing tissue excised from a surgical operation.

4. The method for detecting breast cancer cells according to claim 2, wherein said cell sample is derived from mammilla secretions, punch aspiration tissue samples, mammary duct rinses, sponge biopsy samples of erosive mammilla and mamma areola or smears obtained by pressing tissue excised from a surgical operation.

5. The method for detecting breast cancer cells according to claim 1, wherein said detection is based on in situ hybridization with the probes.

6. The method for detecting breast cancer cells according to claim 2, wherein said detection is based on in situ hybridization with the probes.

7. The method for detecting breast cancer cells according to claim 1, wherein said detection is based on fluorescence in situ hybridization with the probes, and the probes are nucleotide probes having ligands or labels.

8. The method for detecting breast cancer cells according to claim 2, wherein said detection is based on fluorescence in situ hybridization with the probes, and the probes are nucleotide probes having ligands or labels.

9. The method for detecting breast cancer cells according to claim 7, wherein said ligands are biotin, digoxigenin or a mixture thereof and, after the hybridization, the sample is reacted with avidin or anti-digoxigenin antibody labeled with a fluorescent marker.

10. The method for detecting breast cancer cells according to claim 8, wherein said ligands are biotin, digoxigenin or a mixture thereof and, after the hybridization, the sample is reacted with avidin or anti-digoxigenin antibody labeled with a fluorescent marker.

11. The method for detecting breast cancer cells according to claim 7, wherein the probes are labeled with a fluorescent marker selected from the group consisting of fluorescein isothiocyanate, carboxymethyl indocyaninesuccinimidyl ester, rhodamine, sulforhodamine, tetramethylrhodamine isothiocyanate, and 7-amino-4-methylcumarin-3-acetic acid.

12. The method for detecting breast cancer cells according to claim 8, wherein the probes are labeled with a fluorescent marker selected from the group consisting of fluorescein isothiocyanate, carboxymethyl indocyaninesuccinimidyl ester, rhodamine, sulforhodamine, tetramethylrhodamine isothiocyanate, and 7-amino-4-methylcumarin-3-acetic acid.

13. A kit for detecting breast cancer cells, wherein said kit comprises two kinds of probes capable of detecting aneusomy on chromosomes 1 and 11, respectively, of a sample from human breast tissue wherein no additional probes are included other than probes which specifically hybridize with chromosomes 1 and 11.

14. A kit for detecting breast cancer cells, wherein said kit comprises two kinds of probes capable of detecting aneusomy on chromosomes 1 and 17, respectively, of a sample from human breast tissue wherein no additional probes are included other than probes which specifically hybridize with chromosomes 1 and 17.

15. A kit for detecting breast cancer cells, wherein said kit comprises three kinds of probes capable of detecting aneusomy on chromosomes 1, 11 and 17, respectively, of a sample from human breast tissue wherein no additional probes are included other than probes which specifically hybridize with chromosomes 1, 11, and 17.

16. The method as claimed in claim 1, wherein no additional probes are used other than probes which specifically hybridize with chromosomes 1 and 11 or chromosomes 1 and 17.

17. The method as claimed in claim 2, wherein no additional probes are used other than probes which specifically hybridize with chromosomes 1, 11, and 17.

* * * * *